US00PP35730P2

(12) United States Plant Patent
Blaker

(10) Patent No.: US PP35,730 P2
(45) Date of Patent: Apr. 9, 2024

(54) STRAWBERRY PLANT NAMED 'SB_15_089-060'

(50) Latin Name: *Fragaria ananassa*
Varietal Denomination: SB_15_089-060

(71) Applicant: Strawberry Sciences, LLC, Watsonville, CA (US)

(72) Inventor: Kendra M. Blaker, Archer, FL (US)

(73) Assignee: Strawberry Sciences, LLC, Watsonville, CA (US)

( * ) Notice: Subject to any disclaimer, the term of this patent is extended or adjusted under 35 U.S.C. 154(b) by 0 days.

(21) Appl. No.: 18/221,841

(22) Filed: Jul. 13, 2023

(51) Int. Cl.
*A01H 5/08* (2018.01)
*A01H 6/74* (2018.01)

(52) U.S. Cl.
USPC ..... Plt./208

(58) Field of Classification Search
None
See application file for complete search history.

(56) References Cited

U.S. PATENT DOCUMENTS

PP30,564 P3 6/2019 Whitaker

*Primary Examiner* — Susan McCormick Ewoldt
(74) *Attorney, Agent, or Firm* — Foley & Lardner LLP

(57) ABSTRACT

This invention relates to a new and distinct variety of strawberry plant named 'SB_15_089-060'. This new strawberry plant named 'SB_15_089-060' is primarily adapted to the growing conditions of West Central Florida, and is primarily characterized by achenes set even with or slightly below the surface of the fruit; vigorous plant habit; very high marketable yield; early time of first flower and fruit; and very large berry size.

4 Drawing Sheets

Latin name of the genus and species of the plant claimed: *Fragaria ananassa.*

Variety denomination: 'SB_15_089-060'.

BACKGROUND OF THE INVENTION

The present invention relates to a new and distinct strawberry variety named 'SB_15_089-060'. This new variety is a result of a controlled cross made in 2015 in an ongoing breeding program between the unreleased, unpatented strawberry breeding selection designated 'SB_12_104-037' as the seed (female) parent, and the unreleased, unpatented strawberry breeding selection designated 'PS 6.1066' as the pollen (male) parent. The variety is botanically known as *Fragaria ananassa.*

The seedling resulting from the aforementioned cross was selected from a controlled breeding plot in Hillsborough County, Florida in the fall/winter of 2016-2017. After its selection, the new variety was asexually propagated by stolons in both Siskiyou County, California and San Joaquin County, California. The new variety was extensively tested over the next several years in fruiting fields in Hillsborough County, Florida. This propagation has demonstrated that the combination of traits disclosed herein as characterizing the new variety are fixed and remain true-to-type through successive generations of asexual reproduction.

BRIEF SUMMARY OF THE INVENTION

'SB_15_089-060' is primarily adapted to the climate and growing conditions of West Central Florida. The subtropical climate of West Central Florida provides the day length and moderate temperatures needed to produce an early yielding, vigorous plant and maintain fruit quality during the fall and winter production months.

The following traits have been repeatedly observed and are determined to be unique characteristics of 'SB_15_089-060', which in combination distinguish this strawberry plant as a new and distinct variety:

1. Achenes typically set even with or slightly below the surface of the fruit;
2. Vigorous plant habit;
3. Very high marketable yield;
4. Early time of first flower and fruit; and
5. Very large berry size.

'Florida Brilliance' (U.S. Plant Pat. No. PP30,564) is currently the dominant strawberry variety in Hillsborough County, Florida. The fruits of 'SB_15_089-060' are similar in skin integrity and berry shape to 'Florida Brilliance', but the fruit color of 'Florida Brilliance' is slightly lighter than the fruits of 'SB_15_089-060', and the seeds of 'Florida Brilliance' are slightly more sunken than those of 'SB_15_089-060'. The plants of 'SB_15_089-060' are similar in vigor, openness of architecture, and uniformity to 'Florida Brilliance', but have slightly fewer runners per plant than 'Florida Brilliance'. In side-by-side comparisons from the 2022-2023 season (Nov. 21, 2022 to Feb. 24, 2023) 'SB_15_089-060' compares with 'Florida Brilliance' (U.S. Plant Pat. No. PP30,564) in the following combination of characteristics as described in Table 1.

TABLE 1

| Characteristic | 'SB_15_089-060' | 'Florida Brilliance' (U.S. Plant Pat. No. 30,564) |
|---|---|---|
| Nov.-Dec. marketable yield (gm/plt) | 121 | 137 |
| Season marketable yield (gm/plt) | 184 | 303 |

TABLE 1-continued

| Characteristic | 'SB_15_089-060' | 'Florida Brilliance' (U.S. Plant Pat. No. 30,564) |
|---|---|---|
| Nov.-Dec. average berry size (gm) | 22.4 | 17.1 |
| Season average berry size (gm) | 32.9 | 25.3 |

For identification, a series of molecular markers have been determined for this new variety.

'SB_15_089-060' compares with its parents, 'SB_12_104-037' and 'PS 6.1066', by the following combination of characteristics as described in Tables 2 and 3.

TABLE 2

| Characteristic | 'SB_15_089-060' | 'SB_12_104-037' |
|---|---|---|
| Fruit: size | Very Large | Large |
| Fruit: marketable yield | Very High | High |
| Fruit: color | Deep Red | Light Red |
| Plant: vigor | Strong | Moderately Strong |

TABLE 3

| Characteristic | 'SB_15_089-060' | 'PS 6.1066' |
|---|---|---|
| Fruit: size | Very large | Large |
| Fruit: marketable yield | Very high | Medium |
| Plant: foliage density | Moderate | Moderately dense |
| Plant: vigor | Strong | Moderate |

BRIEF DESCRIPTIONS OF THE PHOTOGRAPHS

The accompanying color photographs illustrate the overall appearance of typical specimens of the new strawberry variety 'SB_15_089-060' at various stages of development, as true as it is reasonably possible with color reproductions of this type. Color in the photographs may differ slightly from the color value cited in the botanical descriptions which accurately describe the color of 'SB_15_089-060'. The depicted plant and plant parts of the new strawberry variety 'SB_15_089-060' are approximately four months old. The photographs were taken in Hillsborough County, Florida.

DETAILED BOTANICAL DESCRIPTION

Figure 1:
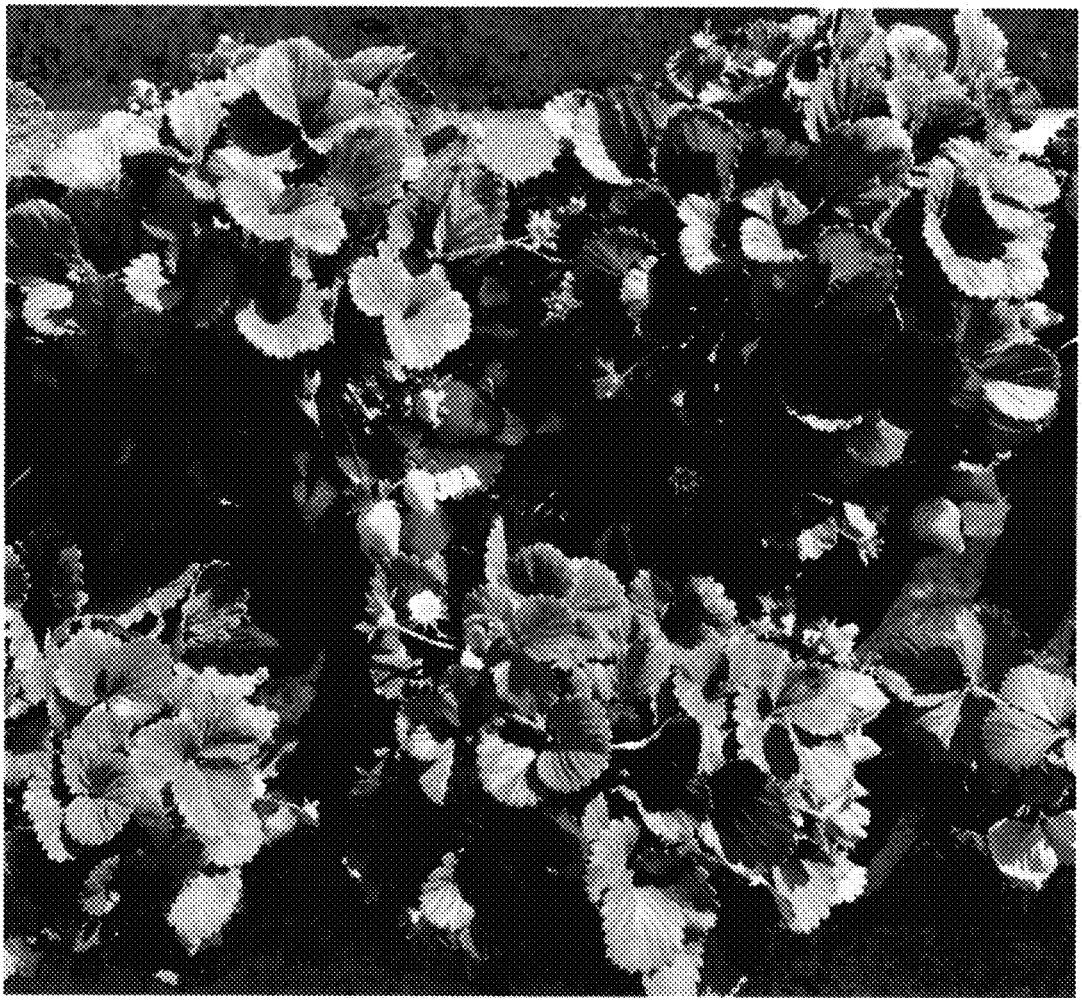
FIG. 1 shows typical fruiting field characteristics of 'SB_15_089-060', taken in the month of February 2023.
Figure 2:
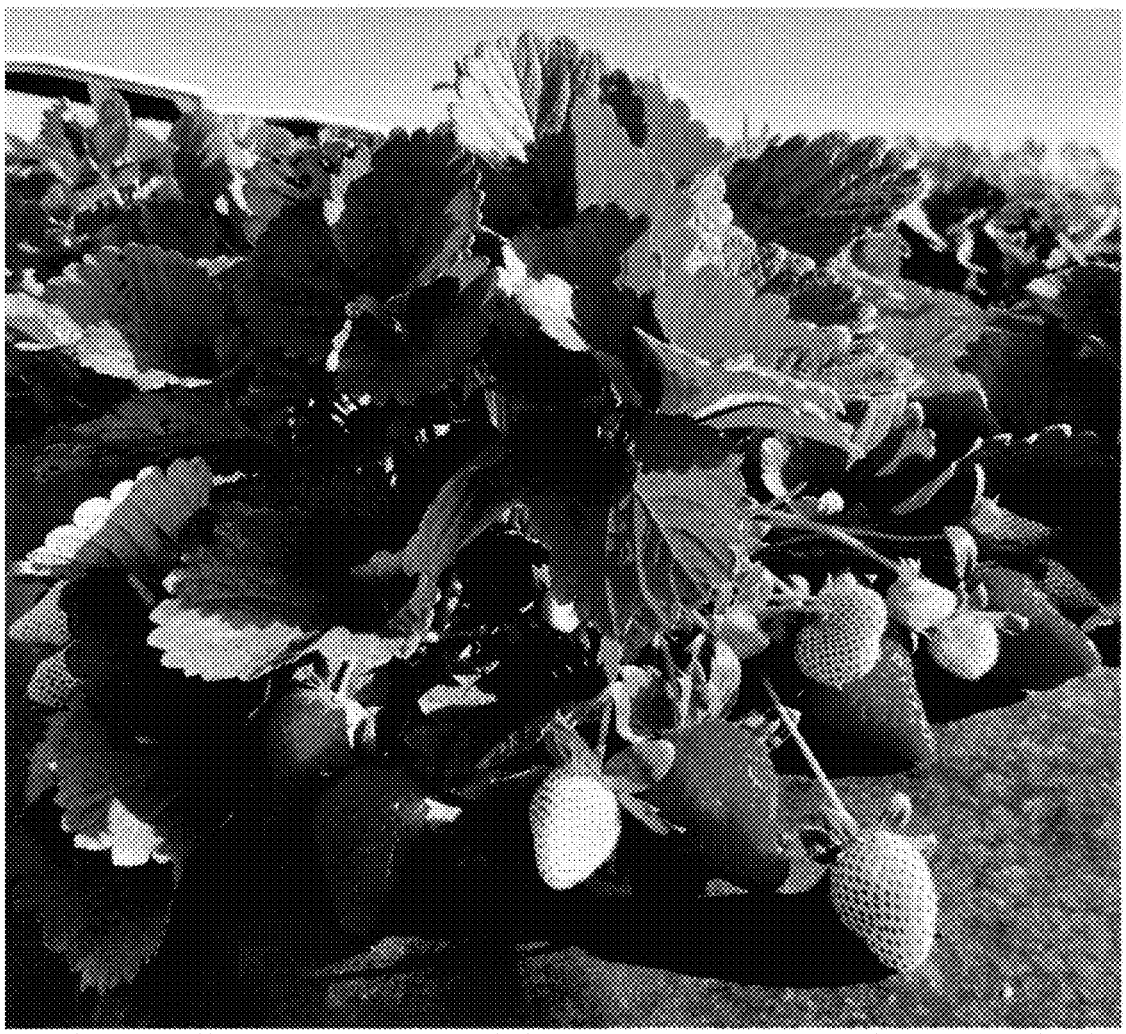
FIG. 2 shows a close-up view of a typical plant of 'SB_15_089-060', taken in the month of February 2023.
Figure 3:
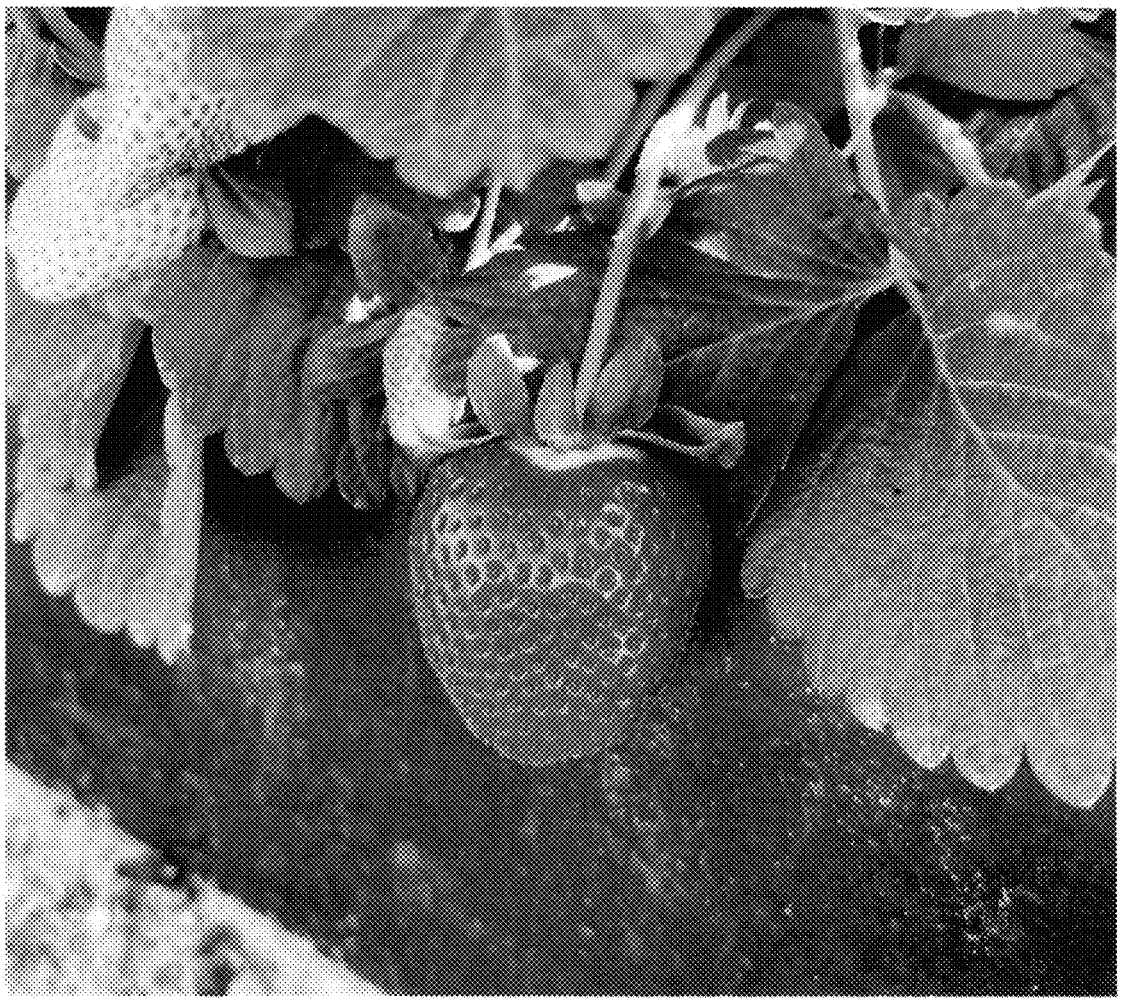
FIG. 3 shows typical mature and immature field fruit of 'SB_15_089-060', taken in the month of February 2023.
Figure 4:
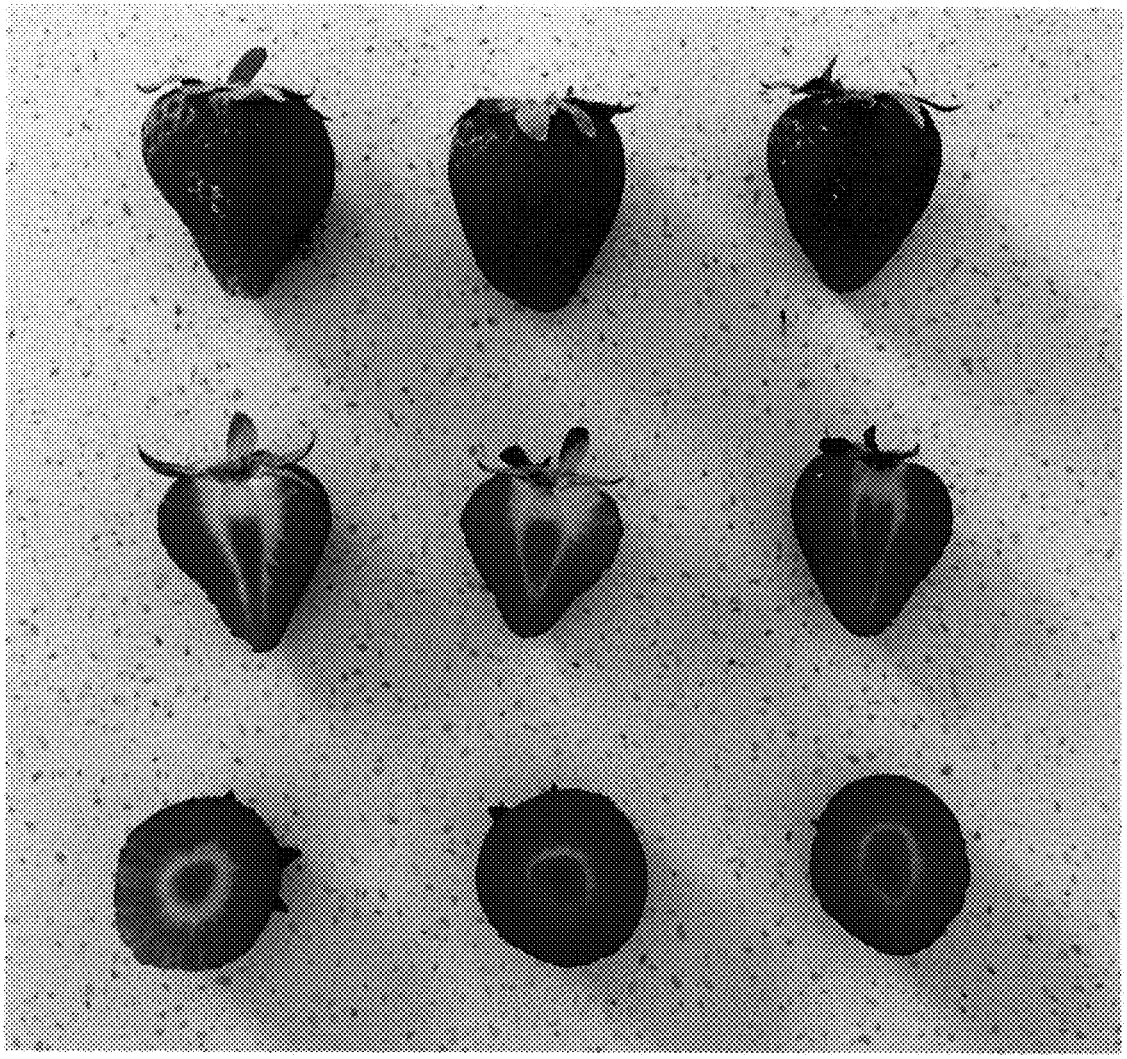
FIG. 4 shows typical internal and external mature fruit characteristics of 'SB_15_089-060', taken in the month of February 2023.

The new variety 'SB_15_089-060' has not been observed under all possible environmental conditions. The characteristics of the new variety 'SB_15_089-060' may vary in detail, depending upon variations in environmental factors, including weather (temperature, humidity and light intensity), day length, soil type and location. In addition, the characteristics of any parental variety or comparison variety included in Table 1 of the present invention may vary in detail, depending upon variations in environmental factors, including weather (temperature, humidity and light intensity), day length, soil type and location.

The aforementioned photographs, together with the following description of the new variety 'SB_15_089-060', unless otherwise noted, are based on observations taken during the 2022-2023 growing season in Hillsborough County, Florida. These measurements and ratings were taken from plants of 'SB_15_089-060' dug from a high-elevation nursery located in Siskiyou County, California during mid-September 2022 and planted approximately four to five days later in Hillsborough County, Florida. The approximate age of the observed plants is four months. Yield observations including average weight and marketable yield, along with fruit quality characteristics including soluble solids, were measured during the 2022-2023 growing season. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2015).

The following characteristics describe fruit, plant, stolon, foliage, fruiting truss, flower, reproductive organs and pest and disease characteristics of the new strawberry 'SB_15_089-060'.

Fruit characteristics:

*Color of mature fruit.*—RHS N45A (red group).

*Color of internal flesh (excluding core).*—RHS 44A (red group).

*Color of core.*—RHS 44A (red group).

*Average length (cm).*—3.9.

*Average width (cm).*—3.6.

*Size.*—Very large.

*Average length/width ratio.*—1.1 (slightly longer than broad).

*Average calyx diameter (cm).*—3.7.

*Season average weight (gm).*—32.9.

*Achene color, shaded side.*—RHS N34A (orange-red group).

*Achene color, sun-exposed side.*—RHS 151B (yellow-green group).

*Average achene weight (mg).*—<2.3.

*Average achenes per berry.*—167.

*Average achene length (mm).*—1.2.

*Average achene width (mm).*—0.9.

*Season marketable yield (gm/plant).*—184.

*Predominant shape.*—Conical.

*Difference in shape between primary and secondary fruit.*—Moderate.

*Band without achenes.*—Ranges from absent to very narrow.

*Evenness of surface.*—Even or very slightly uneven.

*Evenness of color.*—Slightly uneven.

*Glossiness.*—Medium.

*Insertion of achenes.*—Ranges from below surface to even with surface.

*Position of calyx attachment.*—Inserted.

*Attitude of sepals.*—Outward.

*Size of calyx in relation to fruit diameter.*—Slightly larger.

*Adherence of calyx (when fully ripe).*—Strong.

*Firmness of flesh (gf).*—225.

*Distribution of red color of the flesh.*—Marginal and central.
*Hollow center expression.*—Absent or very weak.
*Average cavity length (mm).*—14.01.
*Average cavity width (mm).*—2.14.
*Soluble solids (% Brix).*—7.23.
*Time of first flowering.*—Early (early to mid-October in Hillsborough County, Florida).
*Flowering season.*—October-February.
*Time of first fruit.*—Early (mid-November in Hillsborough County, Florida).
*Fruiting season.*—November-March.
*Post-harvest fruit longevity.*—9-11 days, if stored according to industry standards.
*Type of bearing.*—Not remontant.

Plant characteristics:
*Average height (cm).*—25.5.
*Average spread (cm).*—38.9.
*Size.*—Ranges from medium to large.
*Habit.*—Upright.
*Density.*—Medium.
*Vigor.*—Ranges from medium to strong.

Stolon characteristics:
*Color.*—RHS N144B (yellow-green group).
*Anthocyanin coloration.*—RHS 180C (greyed-red group).
*Anthocyanin intensity.*—Ranges from medium to weak.
*Pubescence.*—Dense.
*Attitude of hairs.*—Slightly outward.
*Average quantity in nursery (per square foot).*—8 (medium.
*Average diameter at the bract (mm).*—2.9 (medium).

Terminal leaflet characteristics:
*Color of upper surface.*—N137A (green group).
*Color of underside.*—RHS 138B (green group).
*Average length (cm).*—8.1.
*Average width (cm).*—8.2.
*Average area terminal ($cm^2$).*—66.0.
*Average length/width ratio.*—0.9 (Ranges from broader than long to as long as broad).
*Shape of base.*—Obtuse.
*Margins (shape of teeth).*—Serrate to crenate.
*Average serrations per leaf.*—18.9.

Foliage characteristics:
*Color of upper surface.*—RHS N137A (green group).
*Color of underside.*—RHS 138B (green group).
*Number of leaflets.*—3.
*Leaf size.*—Medium.
*Average length (cm).*—11.8.
*Average width (cm).*—13.1.
*Average area foliage ($cm^2$).*—153.9.
*Shape in cross section.*—Concave.
*Texture/Interveinal blistering.*—Ranges from medium to absent or weak.
*Leaf glossiness.*—Medium.
*Leaf variegation.*—Absent.
*Venation pattern.*—Pinnate.
*Apex descriptor.*—Obtuse.

Petiole characteristics:
*Petiole color.*—RHS 144B (yellow-green group).
*Average length (cm).*—16.3.
*Average diameter (mm).*—2.8.
*Petiolule color.*—RHS 144A (yellow-green group).
*Petiolule average length (mm).*—10.7.
*Average petiolule diameter (mm).*—1.64.
*Attitude of hairs.*—Strongly outward.
*Texture.*—Smooth.
*Frequency of bract leaflets.*—Ranges from 0 to 2 (70% occurrence).
*Size of bract leaflets.*—Ranges from none to large.
*Pubescence.*—Ranges from moderate to sparse.

Stipule characteristics:
*Color.*—RHS 145D (yellow-green group).
*Anthocyanin coloration.*—RHS 182B (greyed-red group).
*Anthocyanin intensity.*—Weak.
*Average length (mm).*—42.5.
*Average width (mm).*—10.6.
*Base descriptor.*—Truncate.
*Apex descriptor.*—Obtuse.
*Shape.*—Triangular.
*Margin.*—Smooth.
*Texture.*—Smooth.

Fruiting truss characteristics:
*Anthocyanin coloration.*—N/A.
*Anthocyanin intensity.*—Absent.
*Pubescence.*—Weak.
*Attitude at first pick.*—Prostrate.
*Position relative to foliage.*—Ranges from level with to below.
*Flower quantity (average per plant season long).*—49.0 (Ranges from medium to many).
*Average fruits per truss.*—7.1.
*Pedicel attitude of hairs.*—Strongly outward.
*Average pedicel length (cm).*—16.93.
*Average pedicel diameter (mm).*—2.73.
*Pedicel texture.*—Moderate to rough.
*Pedicel color.*—RHS 144B (yellow-green group).
*Average peduncle length (cm).*—6.7.
*Average peduncle diameter (mm).*—3.2.
*Peduncle texture.*—Moderate.
*Peduncle color.*—145B (yellow-green group).

Flower characteristics:
*Flower bud shape.*—Pyriform.
*Average flower bud length (mm).*—19.01.
*Average flower bud diameter (mm).*—8.32.
*Flower bud color.*—RHS 144C (yellow-green group).
*Flower depth (mm).*—5.3.
*Corolla (flower) average diameter (mm).*—29.4 (large).
*Upper petal color.*—RHS NN155B (white group).
*Lower petal color.*—RHS NN155B (white group).
*Petal shape.*—Orbicular.
*Petal apex descriptor.*—Obtuse.
*Petal margin.*—Smooth.
*Petal base.*—Decurrent.
*Petal texture.*—Smooth.
*Petal average length (mm).*—11.6.
*Petal average width (mm).*—11.2.
*Petal average length/width ratio.*—1.03 (longer than broad).
*Average petals per flower.*—5.9.
*Relative position of petals (flowers with 5 or 6 petals).*—Overlapping.
*Upper sepal color.*—RHS 137A (green group).
*Lower sepal color.*—RHS 137D (green group).
*Sepal shape.*—Cuneate.
*Sepal apex descriptor.*—Obtuse.
*Sepal margin.*—Serrate.
*Sepal texture.*—Moderately smooth.

*Sepal average length* (*mm*).—14.2.
*Sepal average width* (*mm*).—5.2.
*Sepal average length/width ratio.*—2.7.
*Average sepals per flower.*—11.4.
*Calyx average diameter* (*mm*).—34.0.
*Size of calyx relative to corolla.*—Larger.
*Size of inner calyx relative to outer calyx.*—Same.

Reproductive organs:

*Receptacle color.*—RHS 147D (yellow-green group).
*Pollen color.*—RHS 17A (yellow-orange group).
*Stamen.*—Present.
*Average filament length* (*mm*).—2.3.
*Filament color.*—RHS 145D (yellow-green group).
*Average anther length* (*mm*).—1.3.
*Anther shape.*—Ovoid.
*Anther color.*—RHS 16A (yellow-orange group).
*Average pistils per flower.*—167.
*Pistil length* (*mm*).—0.5-1.5.
*Style length* (*mm*).—0.5 to 1.
*Style color.*—RHS 10A (yellow group).
*Stigma diameter* (*mm*).—<0.1.
*Stigma shape.*—Simple.
*Ovary color.*—RHS 1C (green-yellow group).
*Pollen amount.*—Abundant.

Disease and pest reactions:

*Colletotrichum crown rot* (*Colletotrichum gloeosporioides*).—Moderately Susceptible.
*Pestalotia leaf spot and fruit rot* (*Neopestalotiopsis sp.*).—Moderately Susceptible.
*Phytophthora crown rot* (*Phytophthora cactorum*).—Susceptible.
*Macrophomina* (*Macrophomina phaseolina*).—Resistant.

We claim:

1. A new and distinct strawberry plant named 'SB_15_089-060', as herein described and illustrated by the characteristics set forth above.

* * * * *